United States Patent [19]

Osher et al.

[11] Patent Number: 5,026,054

[45] Date of Patent: * Jun. 25, 1991

[54] TOY

[75] Inventors: John D. Osher, Shaker Heights, Ohio; Allison W. Katzman, Chicago, Ill.; Mark Luecke, Chicago, Ill.; John R. Wildman, North Riverside, Ill.

[73] Assignee: Cap Toys, Inc., Bedford Heights, Ohio

[*] Notice: The portion of the term of this patent subsequent to Jul. 31, 2007 has been disclaimed.

[21] Appl. No.: 553,582

[22] Filed: Jul. 18, 1990

Related U.S. Application Data

[63] Continuation-in-part of Ser. No. 475,716, Feb. 6, 1990, Pat. No. 4,944,363.

[51] Int. Cl.[5] .............. A63B 37/06; A63B 45/00; A63B 37/08
[52] U.S. Cl. .............. 273/58 A; 273/58 K; 273/DIG. 5; 273/58 J; 273/DIG. 20; 273/424; 446/267; 446/491; 446/385; 446/369
[58] Field of Search .............. 273/58 R, 58 A, 58 C, 273/58 H, 58 J, 58 K, 60 R, 60 B, 61 C, 128 A, 424, 425, DIG. 20, DIG. 29, 26 R, 29 A; 446/46, 47, 48, 267, 491, 369, 380, 382, 385, 390, 391

[56] References Cited

U.S. PATENT DOCUMENTS

| | | | |
|---|---|---|---|
| 1,509,491 | 9/1924 | Sawyer | 273/425 |
| 2,428,827 | 7/1947 | Chagnon | 273/61 |
| 2,484,397 | 10/1949 | Barton | 273/199 R |
| 2,743,931 | 5/1956 | Pooley et al. | 273/60 B |
| 2,753,599 | 7/1956 | Pietraszek et al. | 273/60 B |
| 2,830,402 | 4/1958 | Schleich | 446/385 |
| 2,935,320 | 5/1960 | Chupa | 273/581 |
| 3,238,599 | 3/1966 | Bauman | 446/385 |
| 3,416,800 | 12/1968 | Randall | 273/424 |
| 3,490,770 | 1/1970 | Satchell et al. | 273/231 |
| 3,601,923 | 8/1971 | Rosenberg | 446/267 |
| 3,605,330 | 9/1971 | Sivelle et al. | 446/382 |
| 3,616,101 | 10/1971 | Satchell et al. | 273/231 X |
| 3,676,387 | 7/1972 | Lindlof | 260/28.5 B |
| 3,827,999 | 8/1974 | Crossland | 260/33.6 AQ |
| 3,927,882 | 12/1975 | Galarza | 273/65 E |
| 4,042,057 | 8/1977 | Beckley | 280/751 |
| 4,367,873 | 1/1983 | Chang et al. | 273/60 R |
| 4,369,284 | 1/1983 | Chen | 524/476 |
| 4,463,951 | 8/1984 | Kumasaka et al. | 273/58 A |
| 4,498,667 | 2/1985 | Tomar | 273/60 B |
| 4,618,213 | 10/1986 | Chen | 350/96.34 |
| 4,657,021 | 4/1987 | Perry et al. | 446/267 X |
| 4,772,019 | 9/1988 | Morgan | 273/60 B |
| 4,944,363 | 7/1990 | Osher et al. | 273/58 A |

FOREIGN PATENT DOCUMENTS 1268431  3/1972  United Kingdom ............ 273/58 A Primary Examiner—George J. Marlo
Attorney, Agent, or Firm—Wood, Herron & Evans

[57] ABSTRACT

A resiliently deformable toy ball which is soft and supple and provides an intriguing relaxing feeling when squeezed, and which possesses a low rebound percentage due to its resiliently deformable nature. The ball has a highly plasticized polymeric core which is resiliently deformable due to its highly plasticized state. The polymeric core is encased in a flexible polymer shell and both the core and the flexible shell are further encased in a strechable fabric outer cover.

19 Claims, 2 Drawing Sheets

TOY

This application is a continuation-in-part of application Ser. No. 07/475,716, filed Feb. 6, 1990, and issued as U.S. Pat. No. 4,944,363 on July 31, 1990.

FIELD OF THE INVENTION

The present invention relates to toys, including toy balls, and more particularly to resiliently deformable toys or toy balls which are soft and supple and thereby provide an intriguing relaxing feeling when squeezed, and which also possess a low rebound percentage due to their resiliently deformable nature.

BACKGROUND

Numerous types of toy balls are known which are made of various synthetic materials. For example, U.S. Pat. No. 4,772,019 discloses a composite safety ball having a polyurethane foam core which is designed to replicate the performance of a regulation baseball or softball. U.S. Pat. No. 3,927,882 discloses a soccer ball which has a polyethylene core and an inner nylon cover. U.S. Pat. Nos. 3,616,101 and 3,490,770 disclose liquid center balls, such as golf balls, in which the central portion is a liquid polymer such as polyvinyl chloride. Due to the nature of the materials from which these types of balls are made, and the manner in which they are made, these types of balls are not resiliently deformable to the extent that they would provide a soft, supple feel when squeezed.

Other materials are known which possess resilient or elastomeric properties. For example, U.S. Pat. Nos. 4,369,284 and 4,618,213 are directed to elastomeric gelatinous compounds which may be molded into toy balls. The particular compounds disclosed in the '284 and '213 patents are poly(styrene-ethylene-butylene-styrene) triblock copolymers. While balls made of these types of materials are resilient, they possess an extremely high percentage of plasticizing oil, which tends to bleed or leach out of the ball body. This is undesirable because the user of the ball tends to get plasticizer all over himself and the ball may become brittle and subject to tearing or cracking as it loses plasticizer.

SUMMARY OF THE INVENTION

The present invention is directed to a toy, which in one emobidment may be a toy ball, which has a soft and supple feeling. Preferably, the ball has a highly plasticized polymeric core which is resiliently deformable due to its highly plasticized state and which normally bleeds plasticizer. The highly plasticized core is encased in a flexible polymer shell for containing bleeding of plasticizer from the core, thus protecting the user from exposure to the plasticizer and ensuring that the ball retains its soft and supple resiliency. In a preferred form, both the core and the flexible shell may be further encased in an outer cover. The outer cover, which may be made of any suitable material, is preferably a synthetic fiber material and enhances the "feel" of the ball, protects the core and shell, preventing tearing thereof, and provides the aesthetic appeal of the toy ball of the present invention.

Due to the highly plasticized nature of the polymeric core, the toy ball of the present invention provides a soft and supple resilient feeling to a person holding and squeezing the ball. The feel of the ball is both intriguing and relaxing. In addition, the toy ball has a rebound characteristic which is directly proportional to the height from which the ball is dropped.

A preferred core composition is a highly plasticized polyvinyl chloride (PVC) resin. Alternatively, it is contemplated that other highly plasticized polymeric compounds could be advantageously employed as the core material for the toy ball of the present invention. For example, vinyl halides other than PVC could be used, as could the block and triblock copolymers disclosed in U.S. Pat. Nos. 3,676,387, 4,369,284 and 4,618,213, and other elastomeric materials.

DETAILED DESCRIPTION OF THE INVENTION

Figure 1:
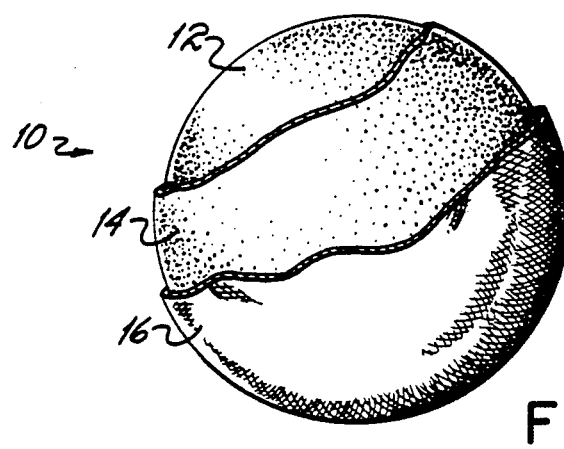
FIG. 1 is a perspective view, partially broken away, of a toy ball embodiment of the toy of the present invention.

FIG. 1 shows a preferred embodiment of the toy ball 10 embodiment of the present invention. Ball 10 comprises a highly plasticized polymeric core 12, a flexible polymer shell 14 encasing core 12, and a stretchable fabric outer cover 16 encasing core 12 and shell 14. The shell is about 0.012 inches thick.

In one preferred embodiment, core 12 is formed from the following components in the percentages indicated:

| | |
|---|---|
| Polyvinyl chloride powder | 25% |
| Di-n-butyl phthalate | 50% |
| Epoxy plasticizer | 10% |
| Stabilizer | 14% |
| Fragrances | 1% |

Di-n-butyl phthalate (DINP) is a plasticizer and thus the total percentage of plasticizer (DINP and epoxy plasticizer) in the core is 60%, in a preferred embodiment. That is, the ratio of plasticizer to PVC is about 2.4:1. The PVC core exhibits a very soft and supple resilient feeling when it is deformed (squeezed) due to its highly plasticized state. This also accounts for the low rebound percentage (about 9%) which characterizes the toy ball of the present invention. As used herein, the phrase "highly plasticized" includes percentages of plasticizer in the core composition to achieve the functional result that the core has a soft and supple resilient feeling when deformed, and a low rebound percentage. It will be appreciated that the specific percentage of plasticizer in the core to achieve the intended functional result will vary depending on the particular polymeric composition and plasticizer. Percentages on a high order of magnitude are contemplated, and may be between about 30%–100%.

The polyvinyl chloride powder used in making the core can be one of any known type, since its specific formulation is not critical to the present invention. Likewise, the stabilizer, the epoxy plasticizer, and the fragrances can each be one of any known such compounds, or combinations thereof, since their specific formulations are also not critical to the present invention. The only criticality in the core composition of this embodiment is that the PVC be highly plasticized to the extent that the toy ball has a low rebound characteristic when dropped and is resiliently deformable. The test procedures and results for rebound and deformability will be described in greater detail below.

It will be appreciated that core 12 may be made from one or a combination of suitable polymeric materials other than PVC, which, when highly plasticized in accordance with the present invention, exhibit the same desired soft, supple, resilient feeling that is exhibited by highly plasticized PVC. Alternative materials categorized under the general heading "vinyl halide resins" are suitable for use in core 12. The term vinyl halide resin, as that term is generally understood in the art, and as intended herein, is used to define those resins or polymers usually derived by polymerization or copolymerization of vinyl halide monomers including vinyl chloride with or without other comonomers such as ethylene, propylene, vinyl acetate, vinyl ethers, vinylidene chloride, methacrylate, acrylates, styrene, etc. The vinyl halide commonly used in the industry is the chloride, although others such as bromide and fluoride may be used.

Elastomers are another suitable type of material that can be employed in core 12 of the toy ball of the present invention. Elastomers are a well known class of polymeric composition including butyl rubbers, ethylene propylene diene terpolymer (EPDM), polysulfide rubber, silicone rubber, neoprene (polychloroprene), chlorosulfonated polyethylene, acrylonitrile-butadiene copolymer (nitrile rubber), styrene butadiene copolymer, acrylonitrile butadiene copolymer-polyvinyl chloride polymer blends, polyisobutylene, polyepichlorohydrin, natural and synthetic polyisoprene, polyvinyl chloride-polybutadiene rubber, polyurethanes, fluorocarbon elastomers such as vinylidene fluoride-chlorobifluoroethylene copolymers, vinylidene-fluoride-hexafluoropropylene copolymers, and fluoroacrylate elastomers as well as others.

Also in a preferred embodiment, flexible shell 14 is comprised of the following:

| Latex | 80% |
|---|---|
| Kaolin | 14% |
| Zinc oxide | 4% |
| Sulfur | 2% |

In one preferred form, flexible shell 14 is relatively thin (i.e., on the order of about 0.012") while being substantially impervious to the plasticizer used in the core. To this end, synthetic latex rubber is preferred over natural rubber since many plasticizers cause the breakdown of natural rubber. Other suitable flexible polymers, such as the elastomers as above identified, can be employed as a shell for core 12 to contain bleeding of plasticizer.

Fabric outer cover 16 is to protect flexible shell 14 and core 12 from tears and the like, and therefore is preferably a substantially tear resistant material that co-acts with core 12 to contain core 12 and shell 14, while at the same time permitting the resilient deformation of the ball.

In a preferred embodiment, the fabric outer cover is comprised of about 80% nylon and about 20% spandex (a two-way stretch fabric) which allows the ball to be resiliently deformed.

By way of example, one embodiment of the toy ball of the present invention, that which has a highly plasticized PVC core, is formed using the following generally known procedures. These procedures are generally applicable to forming toy balls in which materials other than PVC are used. First, the core 12 is cast by mixing the above-listed compounds together and heating them until a molten mixture is formed. subsequently, the molten mixture is poured into a mold having the desired size and shape and allowed to cure for 15–20 minutes. The core is then further cured and cooled by dipping the mold in cold water and the molded core is removed from the mold.

The flexible shell 14 is formed using a procedure known as slush casting. In this procedure, the compounds listed above for the shell (or other suitable compounds) are mixed together by stirring and heated until a molten mixture is formed. Subsequently, the molten mixture is poured into a relatively cold mold so that a layer of the molten compound cures or sets up and forms a "skin" or shell on the mold wall. The thickness of the shell can be varied by varying the temperature of the mold and the length of time the molten material is in the mold. Additionally, the size and shape of the mold are such that the shell formed therein can encase the core formed previously. After a suitable period of time the remaining molten material is poured out of the mold, thus leaving the shell formed and remaining in the mold. The shell is taken out of the mold by blowing the mold with hot air. Then the shell can be placed in an oven and further cured to form the completed shell.

Shell 14 is preferably formed such it has a diameter approximately equal to or slightly greater than that of core 12. Preferably, shell 14 is made with a hole approximately 1" in diameter in the surface thereof or such a hole is cut therein. The flexible shell is then stretched and the core is inserted through the hole. The hole in the shell is then patched with a piece of shell material sufficient to cover the hole glued in place.

Finally, the fabric outer cover 16 which encases core 12 and shell 14 is sewn together therearound. Cover 16 is preferably made from multiple pieces of material of different colors and/or patterns to provide a visually attractive and pleasing look.

As mentioned above, due to the nature of the highly plasticized polymeric core, the toy ball of the present invention is readily resiliently deformable and possesses a low rebound percentage. That is, when squeezed, the ball of the present invention is readily deformed and feels soft and supple. Upon release of the squeezing force, however, the ball virtually immediately returns to its original shape; the ball does not have retarded resiliency as do the articles disclosed in U.S. Pat. No. 2,830,402.

Figure 2:
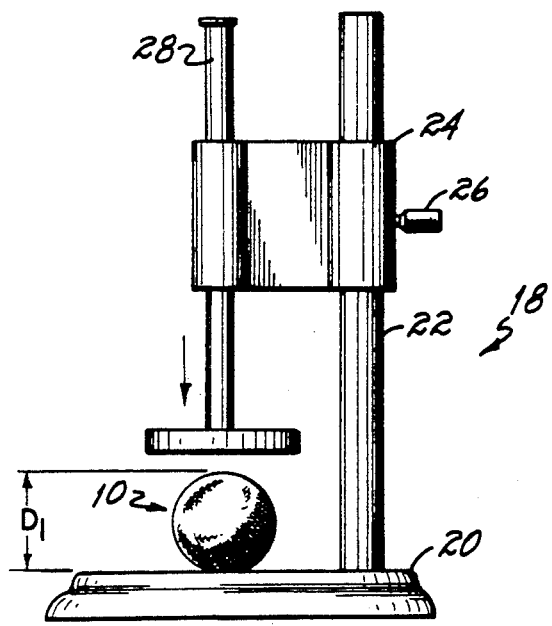
FIG. 2 is a side elevation of a deformability test apparatus with a toy ball positioned for testing.
Figure 3:
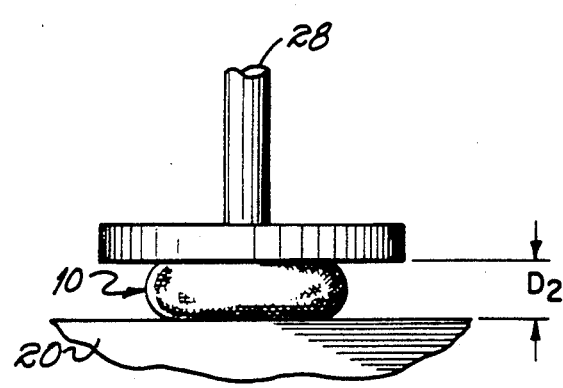
FIG. 3 is an enlarged side elevation of a section of the apparatus shown in FIG. 2, with the toy ball deformed.

FIG. 2 shows a test apparatus 18 for testing the resilient deformability of toy ball 10. Test apparatus 18 includes a rigid base 20 upon which toy ball 10 is placed for testing purposes. Additionally, test apparatus 18 includes an upstanding shaft 22 having a vertically slidably adjustable bracket 24 positioned thereon. Bracket 24 can be secured at a desired vertical level by tightening thumb screw 26. Bracket 24 has an aperture therethrough slidably receiving weighted plunger 28, which is used to deform toy ball 10. As can be seen in FIG. 2, plunger 28 is positioned vertically above toy ball 10 prior to testing the deformability of the ball. Ball 10 has a first diameter designated as $D_1$ in FIG. 2 when the ball is not deformed by any external forces or pressure. When the weight of plunger 28 is allowed to deform ball 10, as shown in FIG. 3, ball 10 takes on a new diameter $D_2$, as measured in the vertical direction in FIG. 3.

In a preferred embodiment of the toy ball of the present invention in which core 12 includes highly plasticized PVC, $D_1$ is between about 60–67 mm and the ball weighs approximately 150 grams. $D_2$, which is a function of the weight of the plunger, and the length of time the weight is exerted on the ball, is preferably about 33 mm when plunger 28 weighs about 1850 g and has exerted its weight on ball 10 for approximately 2 seconds or less. Thus $D_2$ equals $\frac{1}{2}D_1$ when the weight ratio of the plunger to the ball is about 12.5:1. This test apparatus thereby measures the initial deformation of toy ball 10 by a known force in a defined time period, and disregards the subsequent or further deformation or relaxation of toy ball 10 which may occur if plunger 28 is left to rest on toy ball 10 for longer periods of time.

A preferred embodiment of the toy ball of the present invention was tested for its rebound percentage or characteristic when dropped from a known height onto a rigid surface. Ball 10 was repeatedly dropped from a height of 36" and rebounded between about 3"–3½", for an average of about 9%. Ball 10 was then repeatedly dropped from heights of 48" and 60" to determine if the correlation between the rebound 48", ball 10 rebounded between about 4–4¼", for an average of about 9%, and from 60", ball 10 rebounded about 5–5½", also for an average of about 9%. It was therefore determined that the correlation between the height of the drop and the rebound percentage is generally substantially linear. Both the rebound and deformability tests were conducted at room temperature.

Figure 4:
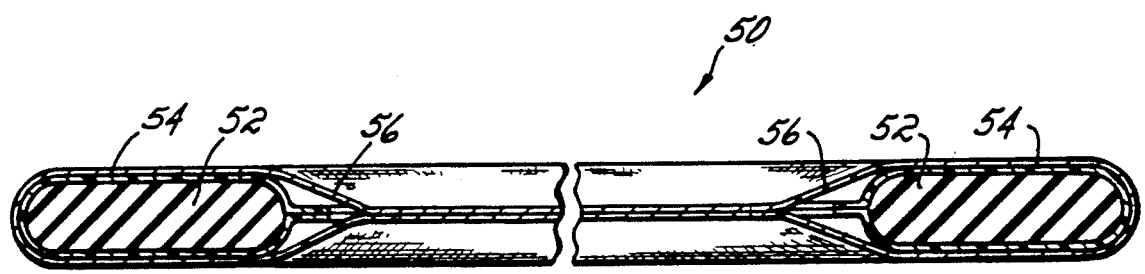
FIG. 4 is a cross section of an alternative embodiment of the toy of the present invention.

FIG. 4 is a cross-sectional view of an alternative toy embodiment of the present invention. FIG. 4 shows a flying disc-type toy 50 that includes an annular core 52, which is preferrably a highly plasticized polymeric material such as is described hereinabove with respect to the toy ball embodiment. Annular core 52 is encased in a flexible polymer shell 54 to contain bleeding of plasticizer from core 52. Both the core 52 and shell 54 are preferrably further encased in a stretchable fabric outer cover, also as described hereinabove.

It will be appreciated that the present invention need not and is not limited to toy balls and toy flying discs and in fact encompasses all types of articles having a highly plasticized polymeric core which is resiliently deformable, a flexible shell encasing the core, and a stretchable fabric outer cover encasing the core and flexible shell.

What is claimed is:

1. A toy ball having a soft and supple feeling, comprising:
   a highly plasticized polymeric core which is resiliently deformable due to its highly plasticized state and normally bleeds plasticizer; and
   a flexible polymer shell encasing said core for containing bleeding of said plasticizer from said core.

2. The toy ball of claim 1 further comprising:
   a stretchable fabric outer cover encasing said core and said flexible shell.

3. The toy ball of claim 1 wherein said core contains highly plasticized polyvinyl chloride.

4. The toy ball of claim 3 wherein said core contains about 25% polyvinyl chloride and at least about 60% plasticizer.

5. The toy ball of claim 4 wherein said core further contains a stabilizer compound and a fragrance compound.

6. The toy ball of claim 1 wherein said flexible polymer shell includes about 80% latex, 14% kaolin and 4% zinc oxide, said shell being substantially impervious to said plasticizer.

7. The toy ball of claim 1 wherein said stretchable fabric outer cover is about 80% nylon and about 20% spandex.

8. A toy ball having a soft and supple feeling, comprising:
   a highly plasticized polymeric core which is resiliently deformable due to its highly plasticized state and normally bleeds plasticizer;
   a flexible polymer shell encasing said core for containing bleeding of said plasticizer from said core; and
   a stretchable fabric outer cover encasing said core and said flexible shell.

9. A toy ball having a soft and supple feeling, comprising:
   a highly plasticized polymeric core which is resiliently deformable due to its highly plasticized state and normally bleeds plasticizer;
   a flexible polymer shell encasing said core for containing bleeding of said plasticizer from said core; and
   a stretchable fabric outer cover encasing said core and said flexible shell;
   said toy ball being characterized by a soft, supple, resilient feeling, is readily deformable and pliable, and substantially returns to its original shape after a deforming force is removed.

10. The toy ball of claim 9 wherein said ball has a weight $W_1$, and has a first diameter $D_1$ when no external forces on exerted on said ball and a second diameter $D_2$ when the force of a test weight $W_2$ is exerted on said ball for about two seconds, $D_2$ is about $\frac{1}{2}D_1$, when $W_2$ is about $12.5W_1$.

11. The toy ball of claim 10 wherein $W_1$ is about 150 grams, $W_2$ is about 1850 grams, $D_1$ is between 60–67 mm, and $D_2$ is about 33 mm.

12. The toy ball of claim 9 wherein the ball has a rebound percentage which is directedly proportional to the height from which the ball is dropped.

13. The toy ball as claimed in claim 12 wherein the ball as a rebound percentage of about 9%.

14. A toy comprising:
   a highly plasticized polymeric core which is resiliently deformable due to it highly plasticized state and normally bleeds platicizer;
   a flexible polymer shell encasing said core for containing bleeding of said plasticizer from said core; and
   a stretchable fabric outer cover encasing said core and said flexible shell.

15. A toy comprising:
   a highly plasticized polymeric core which is resiliently deformable due to its highly plasticized state and normally bleeds plasticizer;
   a flexible polymer shell encasing said core for containing bleeding of said plasticizer from said core, said toy being characterized by a soft supple, resilient feeling, is readily deformable and pliable and substantially returns to its original shape after a deforming force is removed.

16. A toy as claimed in claim 15 further comprising a stretchable fabric outer cover encasing the core and the flexible shell.

17. A toy as claimed in claims 15 or claim 17 wherein the core contains highly plasticized polyvinyl chloride.

18. A toy as claimed in claim 16 wherein the stretchable fabric outer cover is about 80% nylon and 20% spandex.

19. A toy as claimed in claim 15 wherein the core contains about 25% polyvinyl chloride and at least about 60% plasticizer.

* * * * *

UNITED STATES PATENT AND TRADEMARK OFFICE
CERTIFICATE OF CORRECTION

PATENT NO. :     5,026,054

DATED      :     June 25, 1991

INVENTOR(S) :    John D. Osher et al.

It is certified that error appears in the above-identified patent and that said Letters Patent is hereby corrected as shown below:

Column 5, line 27, after "rebound" insert --percentage and the height of the drop is linear. From--

Column 5, line 28, "4¼" should be --4½--

Column 7, line 4, "17" should be --16--

Signed and Sealed this

Twelfth Day of January, 1993

*Attest:*

DOUGLAS B. COMER

*Attesting Officer*     Acting Commissioner of Patents and Trademarks